United States Patent
Chen

(10) Patent No.: US 10,258,499 B2
(45) Date of Patent: Apr. 16, 2019

(54) KNEADING MOXIBUSTION DEVICE

(71) Applicant: Kuang-Hou Chen, New Taipei (TW)

(72) Inventor: Kuang-Hou Chen, New Taipei (TW)

( * ) Notice: Subject to any disclaimer, the term of this patent is extended or adjusted under 35 U.S.C. 154(b) by 1143 days.

(21) Appl. No.: 14/584,135

(22) Filed: Dec. 29, 2014

(65) Prior Publication Data

US 2016/0184173 A1 Jun. 30, 2016

(51) Int. Cl.
  *A61H 7/00* (2006.01)
  *A61F 7/00* (2006.01)
  *A61H 39/06* (2006.01)

(52) U.S. Cl.
  CPC ............ *A61F 7/007* (2013.01); *A61H 7/007* (2013.01); *A61F 2007/0071* (2013.01); *A61F 2007/0087* (2013.01); *A61H 39/06* (2013.01); *A61H 2201/0153* (2013.01); *A61H 2201/0207* (2013.01); *A61H 2201/0228* (2013.01); *A61H 2201/1253* (2013.01); *A61H 2201/1284* (2013.01); *A61H 2201/1695* (2013.01); *A61H 2203/0456* (2013.01); *A61H 2205/081* (2013.01); *A61H 2205/12* (2013.01)

(58) Field of Classification Search
  CPC ............ A61H 2201/1253; A61H 7/007; A61H 39/06; A61F 7/007; A61F 2007/0071
  USPC .............. 607/96–99, 103; 219/236, 229, 601
  See application file for complete search history.

(56) References Cited

U.S. PATENT DOCUMENTS

| | | | | | |
|---|---|---|---|---|---|
| 2,021,732 | A | * | 11/1935 | Lipsner | A61H 15/02 219/533 |
| 2,280,367 | A | * | 4/1942 | Barton | H05B 3/46 338/241 |
| 4,082,089 | A | * | 4/1978 | Moriyama | A61F 7/007 601/19 |
| 4,502,469 | A | * | 3/1985 | Jaw | A61B 18/08 601/15 |
| 4,745,264 | A | * | 5/1988 | Carter | B23K 3/0475 219/229 |
| 5,374,284 | A | * | 12/1994 | Guibert | A61F 7/00 607/96 |
| 5,425,731 | A | * | 6/1995 | Daniel | A61B 18/082 219/229 |
| 2002/0143374 | A1 | * | 10/2002 | Tai | A61F 7/00 607/96 |

(Continued)

*Primary Examiner* — Colin W Stuart
*Assistant Examiner* — Douglas Y Sul
(74) *Attorney, Agent, or Firm* — Bacon & Thomas, PLLC

(57) ABSTRACT

The present invention is to provide a kneading moxibustion device, which includes a base having one end provided with a receiving cavity; a contact element made of an insulting material for sealing the cavity; a control circuit mounted inside the cavity for generating a driving signal according to electricity received; a coil tube positioned inside the cavity and including a heating coil with a plurality of turns wound around a hollow insulating member for receiving the driving signal; and a conducting element formed of metal and including an induction portion inserted into the insulating member and a conduction portion having one end connected to the induction portion and an opposite end against the contact element; so that the heating coil can generate a precise thermal energy in response to the driving signal and then transfer the thermal energy to a user's body through the conducting element and contact element sequentially.

4 Claims, 5 Drawing Sheets

(56) References Cited

U.S. PATENT DOCUMENTS

| | | | | |
|---|---|---|---|---|
| 2003/0155225 A1* | 8/2003 | Kondo | ............... | H01H 9/18 |
| | | | | 200/570 |
| 2011/0319818 A1* | 12/2011 | Shimada | ............ | A61F 7/007 |
| | | | | 604/114 |
| 2014/0058277 A1* | 2/2014 | Tan | ............ | A61B 5/028 |
| | | | | 600/487 |
| 2014/0323929 A1* | 10/2014 | Iurchenko | ............ | A61H 19/40 |
| | | | | 601/46 |

* cited by examiner

KNEADING MOXIBUSTION DEVICE

FIELD OF THE INVENTION

The present invention is to provide a kneading device, more particular to a kneading moxibustion device capable of generating a thermal energy in a precise temperature range (e.g., 40~50° C.) and uniformly and indirectly transferring the thermal energy to a user's body for effectively increasing the convenience and efficacy of moxibustion.

BACKGROUND OF THE INVENTION

Recently, with the rapid development of economy, people are getting better off and, instead of striving to meet only the basic needs, have placed more and more importance on the quality of life, of which health care is an essential aspect. In the meantime, however, work pressure is increasing with the tempo of modern life, and failure to properly relax the body and mind often leads to physical and/or mental problems, causing illnesses and discomfort. While many people resort to massage or tui na for relaxation, neither of them can be practiced by an amateur on themselves with satisfactory results, for both therapies rely on the accurate application of a manual kneading force to stimulate the acupoints and regulate bodily functions.

In traditional Chinese medicine, "acupuncture, moxibustion, medication, cupping, and tui na" are collectively known as the five major therapies, wherein moxibustion is carried out by burning medicinal herbs and conducting the thermal energy thus generated into certain acupoints via the skin so as to alleviate pain and trigger the immune system through the stimulation of heat. The moxibustion therapy not only can effectively relieve fatigue but also has significant regulatory effects on blood pressure, respiration, pulses, heart rate, blood vessels, and the nervous system. As moxibustion does not require the use of needles for acupoint stimulation as does acupuncture, the former has higher public acceptance than the latter and is becoming increasingly popular.

In moxibustion, it is mainly the thermal energy that stimulates and excites the channels, network vessels, and acupoints in the body, and yet the thermal energy required is not necessarily generated by "burning medicinal herbs". Currently, the market is supplied with moxibustion devices which generate thermal energy by electric heating and which can also be used to knead the desired spots of the user's body so that massage and tui na can be performed together with moxibustion with the assistance of heat. Please refer to FIG. 1 for a conventional moxibustion device 1 which includes a holding portion 11, a light bulb-based heat source unit 12, and a heat accumulating portion 13. The holding portion 11 is a hollow tube and is provided therein with a lamp base 110 on which the light bulb-based heat source unit 12 is mounted. The heat accumulating portion 13 covers the end of the holding portion 11 that corresponds to the light bulb-based heat source unit 12. When the light bulb-based heat source unit 12 is supplied with electricity, it projects light, and thereby transfers thermal energy, to the heat accumulating portion 13, and the moxibustion device 1 can be used in this state to knead and massage the desired spots of the body.

However, consumers' willingness to use the moxibustion device 1 and the like tends to be reduced by the following drawbacks in design, which cause inconvenience in use:

(1) Inefficient heat transfer: The moxibustion device 1 in FIG. 1 generates thermal energy through the light bulb-based heat source unit 12, which nevertheless generates both light and thermal energy when supplied with electricity. In fact, a major part of the electric energy received by the light bulb-based heat source unit 12 is converted into light; only the remaining part is converted into thermal energy. That is to say, the moxibustion device 1 has low conversion efficiency in terms of thermal energy. Besides, the light bulb-based heat source unit 12 is not in contact with the heat accumulating portion 13, so thermal energy generated by the light bulb-based heat source unit 12 can be transferred to the heat accumulating portion 13 only by radiation (i.e., through light) or convection (i.e., through air). In either case, however, partial loss of the thermal energy is inevitable during the transfer process. It can be known from the above that the heat generation mechanism of the moxibustion device 1 leaves much to be desired, especially with regard to conversion and transfer efficiency.

(2) High power consumption: Apart from the moxibustion device 1 shown in FIG. 1, moxibustion devices which generate heat through electric heating wires or plates are also available. Such electric heating wires or plates, however, consume a staggeringly large amount of electricity per unit time. This exceptionally high power consumption not only dampens the general public' willingness to purchase like products but also hinders product promotion and sales.

(3) Non-uniform temperature distribution: As moxibustion requires pressing each desired spot of the body for a certain period of time, "temperature" and "uniform distribution of thermal energy" are key to the therapy results. Taking the moxibustion device 1 in FIG. 1 for example, the heat accumulating portion 13 is made of metal and can therefore rapidly transfer the thermal energy generated by the light bulb-based heat source unit 12 to the desired spots of the body, but if power control in the moxibustion device 1 is instable, resulting in excessively high thermal energy, the user is subject to burn damage. Some moxibustion devices have a housing made of an insulating material, whose low thermal conductivity, however, can lead to non-uniform distribution of thermal energy or failure to maintain the predetermined temperature for a long time.

Hence, the issue to be addressed by the present invention is to design a kneading moxibustion device which not only takes into account the conduction and conversion efficiency of thermal energy but also can output thermal energy stably while used for moxibustion.

BRIEF SUMMARY OF THE INVENTION

In view of the drawbacks of the existing moxibustion devices, particularly the low thermal energy conversion and transfer efficiency and the incapability to maintain a uniform distribution of heat, the inventor of the present invention incorporated years of practical experience into research and repeated tests and improvements and finally succeeded in designing a kneading moxibustion device as disclosed herein for overcoming the aforesaid drawbacks effectively.

It is an objective of the present invention to provide a kneading moxibustion device which includes a base, a contact element, a control circuit, a coil tube, and a conducting element. The base is concavely provided with a receiving cavity at one end and is further provided with a first assembly portion adjacent to the receiving cavity. The contact element is made of an insulting material (e.g., a wood moxibustion head) and is provided with a second assembly portion at one end. The second assembly portion can be connected with the first assembly portion (e.g., by projection-recess engagement or threaded connection) so that the contact element seals the receiving cavity and a sealed space is formed as a result. The control circuit is mounted in the receiving cavity and can electrically connect with a power supply unit (e.g., a power socket or a battery) in order to receive the electricity provided by the power supply unit and generate a driving signal according to the electricity received. The coil tube is positioned in the sealed space and includes an insulating member and a heating coil with a plurality of turns. The insulating member is hollow. The heating coil is wound around the insulating member and is electrically connected to the control circuit in order to receive the driving signal. When the driving signal is a direct current, the heating coil generates thermal energy in response to the direct current running through the heating coil. The conducting element is formed of metal and includes an induction portion and a conduction portion. The configuration of the induction portion matches that of the insulating member in order for the induction portion to be inserted into the insulating member and consequently correspond in position to the heating coil. One end of the conduction portion is connected to the induction portion while the opposite end of the conduction portion lies against an inner wall surface of the contact element. This arrangement allows the thermal energy generated by the heating coil to be transferred to an outer surface of the contact element sequentially through the insulating member, the induction portion, and the conduction portion. According to the present invention, thermal energy is generated by a coil and transferred indirectly through the conducting element to the user's body. Therefore, not only are such advantages as low power (about 2~5 W) and high conversion efficiency achieved, but also a uniform distribution of thermal energy over the contact element and a precise temperature range (e.g., 40~50° C.) are ensured to effectively increase the convenience and efficacy of moxibustion.

Another objective of the present invention is to provide the foregoing kneading moxibustion device, wherein the driving signal of the control circuit can also be an alternating current. When the alternating current runs through the heating coil, an alternating magnetic field is created in the sealed space such that an induced current is generated in the induction portion of the conducting element. The conducting element generates heat due to the induced current and transfers the heat to the contact element.

BRIEF DESCRIPTION OF THE SEVERAL VIEWS OF THE DRAWINGS

The technical principle, structural features, and objectives of the present invention will be best understood by referring to the following detailed description of some illustrative embodiments in conjunction with the accompanying drawings, in which.

DETAILED DESCRIPTION OF THE INVENTION

Figure 2:
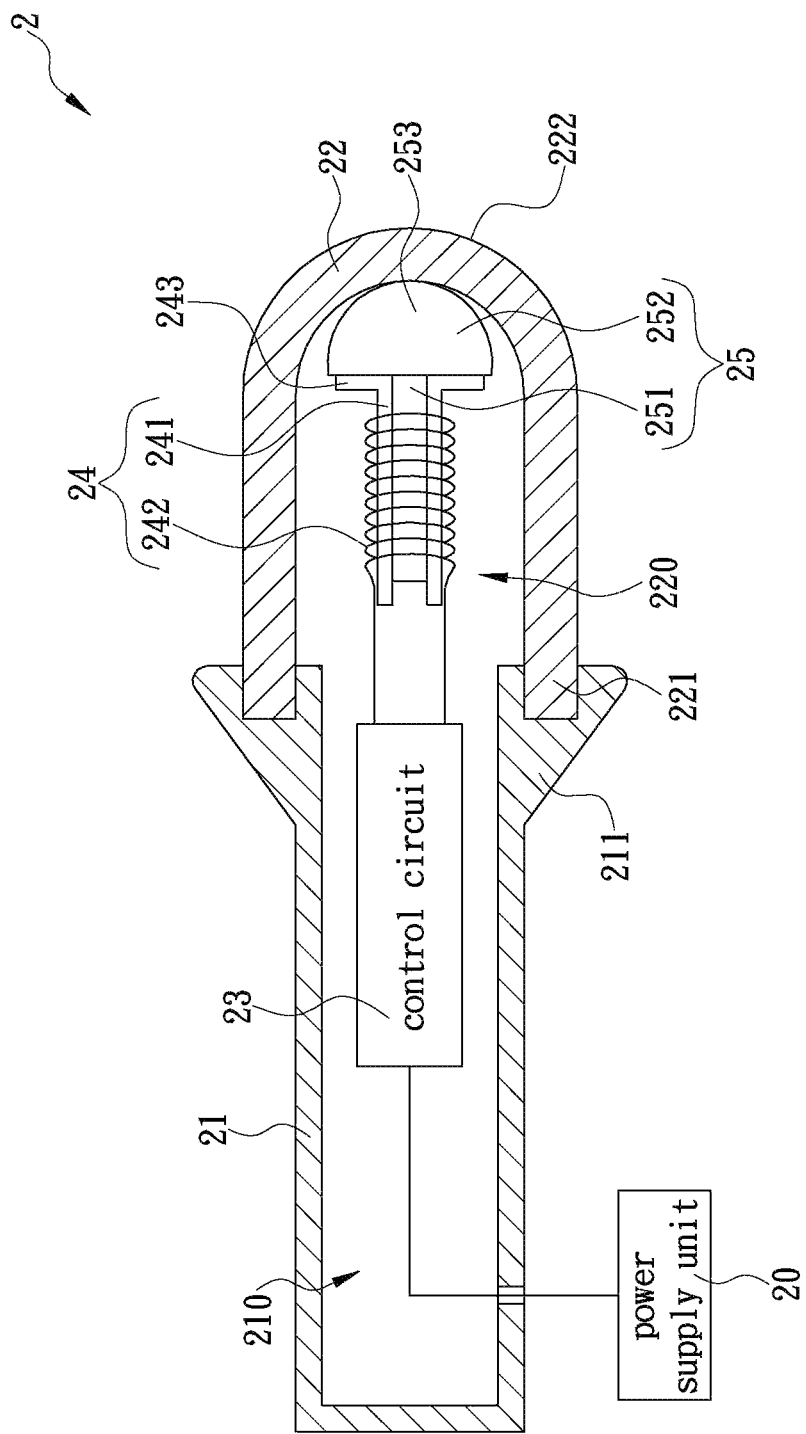
FIG. 2 schematically shows the first preferred embodiment of the kneading moxibustion device of the present invention.

The present invention provides a kneading moxibustion device. Referring to FIG. 2 for the first preferred embodiment of the present invention, the kneading moxibustion device 2 includes a base 21, a contact element 22, a control circuit 23, a coil tube 24, and a conducting element 25. The base 21 is concavely provided with a receiving cavity 210 at one end and is peripherally provided with a first assembly portion 211 adjacent to the receiving cavity 210. The contact element 22 is made of an insulating material (e.g., wood as in this embodiment, though any non-metal insulating material can be used just as well) and is configured as a hollow cover. The contact element 22 is peripherally provided with a second assembly portion 221 at one end and is further provided with a curved contact surface 222 at the opposite end. In this embodiment, the first assembly portion 211 is a groove, and the second assembly portion 221 is a post to be fixed in the first assembly portion 211 by a tight fit therebetween so that a sealed space is formed between the hollow interior of the contact element 22 and the receiving cavity 210. In other preferred embodiments of the present invention, however, the configurations of the assembly portions 211 and 221 are not limited to the above. For instance, the assembly portions 211 and 221 can be connected to each other by threaded connection, projection-recess engagement, and so on.

The control circuit 23 is mounted in the receiving cavity 210 and can be electrically connected to a power supply unit 20 (e.g., a power socket or a battery) in order to receive the electricity provided by the power supply unit 20 and generate a driving signal according to the electricity received. The coil tube 24 is positioned in the sealed space 220 and includes an insulating member 241 and a heating coil 242 having a plurality of turns. In this embodiment, the insulating member 241 is hollow and is provided with a stop portion 243 at one end. The heating coil 242 is wound around the middle section of the insulating member 241 and is electrically connected to the control circuit 23 in order to receive the driving signal.

The conducting element 25 is formed of metal and includes an induction portion 251 and a conduction portion 252. The induction portion 251 matches the insulating member 241 in configuration so as to be inserted into the insulating member 241 and consequently correspond in position to the heating coil 242. One end of the conduction portion 252 is connected to the induction portion 251 and, with a cross-sectional width matching the length of the stop portion 243, lies against the stop portion 243. The opposite end of the conduction portion 252 (hereinafter referred to as the second end of the conduction portion 252) is provided with a curved conducting surface 253. The configuration of the curved conducing surface 253 matches that of the curved contact surface 222 in such a way that the second end of the conduction portion 252 lies tightly against an inner wall surface of the contact element 22, allowing the thermal energy generated by the heating coil 242 to be transferred sequentially through the insulating member 241, the induction portion 251, and the conduction portion 252 to an outer surface of the contact element 22.

Figure 1:
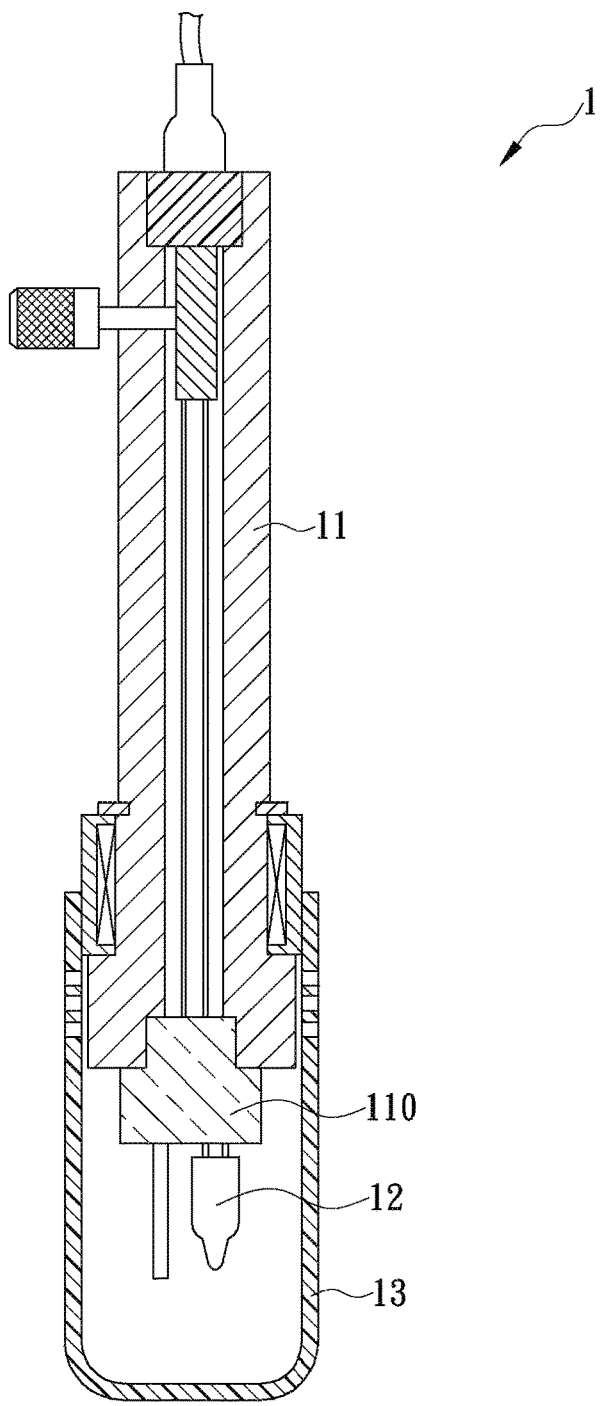
FIG. 1 schematically shows a conventional kneading moxibustion device.

The kneading moxibustion device 2 of the present invention can operate on both direct current and alternating current, as detailed below. When the driving signal is a direct current, the heating coil 242 with multiple turns exhibits certain electrical resistance not to be ignored (the electrical resistance of a conductive wire can be calculated by the equation: "resistance=total wire length×wire resistivity/cross sectional area of wire", i.e., $R=L×\rho/A$), and the power of the heating coil 242 can be determined by the equation: "power=square of supplied voltage/resistance", i.e., $P=V^2/R$. According to tests conducted by the inventor, in which the driving signal provides a constant 12-V voltage and the heating coil 242 has 1500 turns (in the preferred embodiments of the present invention, a temperature suitable for moxibustion can be generated when the heating coil 242 has 500~2500 turns), the current in the heating coil 242 is about 0.2 mA, and the power of the heating coil 242 is about 4~5 W, which is far lower than that of the conventional light bulb-based heat source unit 12 shown in FIG. 1 (the power of a common incandescent light bulb is about 70~100 W). Meanwhile, the temperature of the heating coil 242 is about 50° C., and the temperature of the outer surface of the contact element 22 is about 45° C., with a uniform distribution of thermal energy. The overall loss of thermal energy is nominal.

When the driving signal is an alternating current, on the other hand, operation of the heating coil 242 follows the equation: "inductive reactance=2×π×frequency of driving signal×inductance" and the electromagnetic induction equations: "$\Phi_B=\iint\Sigma_{(t)}B(r,t)\cdot dA$" and "$\varepsilon=-d\Phi_B/dt$". In other words, when an alternating current flows through the heating coil 242, the heating coil 242 generates an alternating magnetic field in the sealed space 220 according to current variation. As the magnetic lines in the alternating magnetic field cause a significant change in magnetic flux in the conducting element 25, an induced current is generated in the conducting element 25 due to electromagnetic induction. Thus, the conducting element 25 generates thermal energy.

In summary, when the driving signal is a direct current, the heating coil 242 generates thermal energy in response to the direct current passing through the heating coil 242; when the driving signal is an alternating current, the heating coil 242 generates an alternating magnetic field in the sealed space 220 in response to the alternating current passing through the heating coil 242. The heating coil 242 can therefore heat the induction portion 251 of the conducting element 25 via either thermal conduction or electromagnetic induction, and in either case, thermal energy is transferred through the insulating member 241, the induction portion 251, and the conduction portion 252 to the outer surface of the contact element 22. As such, the kneading moxibustion device 2 achieves the following advantageous effects:

(1) Uniform heat transfer: As the thermal energy generated by the coil tube 24 is transferred indirectly through the metallic conducting element 25 to the contact element 22, which is made of an insulating material, it is ensured that the outer surface of the contact element 22 has a uniform distribution of temperature, undergoes slow heat dissipation, and can therefore stay within a temperature range suitable for moxibustion (i.e., 40~50° C.) for a long time. In addition, referring to FIG. 2, although the thermal energy in the contact element 22 is concentrated at the position of contact between the contact element 22 and the conducting element 25 (i.e., the tip of the contact element 22), the thermal energy generated by the coil tube 24 is guided to other parts of the contact element 22 as well through the air in the sealed space 220. As a result, the lateral side of the contact element 22 also has a certain degree of warmth, which imparts a larger moxibustion area to the kneading moxibustion device 2 than those of the prior art devices.

(2) Efficient thermal conduction: With both the coil tube 24 and the conducting element 25 sealed in the sealed space 220, loss of thermal energy is minimized during heat transfer, and the excellent thermal conductivity of the kneading moxibustion device 2 is demonstrated by the foregoing test result that the temperature of the outer surface of the contact element 22 stays as high as about 45° C. when the temperature of the heating coil 242 is 50° C.

(3) Low power: Compared with the kneading moxibustion device 1 shown in FIG. 1, the present invention uses the coil tube 24 for heating and does not require projection of light. Therefore, high energy efficiency is achieved, and a low-power (about 2~5 W) power supply will suffice. Moreover, referring to FIG. 2, the low power requirement of the present invention makes it feasible to connect a USB connector to the control circuit 23 through a transmission cable. Thus, the user only has to connect the USB connector to a USB port of an electronic device (e.g., a personal computer or laptop computer) that can provide a constant 5-V voltage, and moxibustion can be carried out with ease anywhere anytime.

(4) Compact structure: In the present invention, both the coil tube 24 and the conducting element 25 are of very simple configurations and do not take up too much space, and because of that, the kneading moxibustion device 2 can be designed to be as thin as a finger to facilitate holding.

Figure 3:
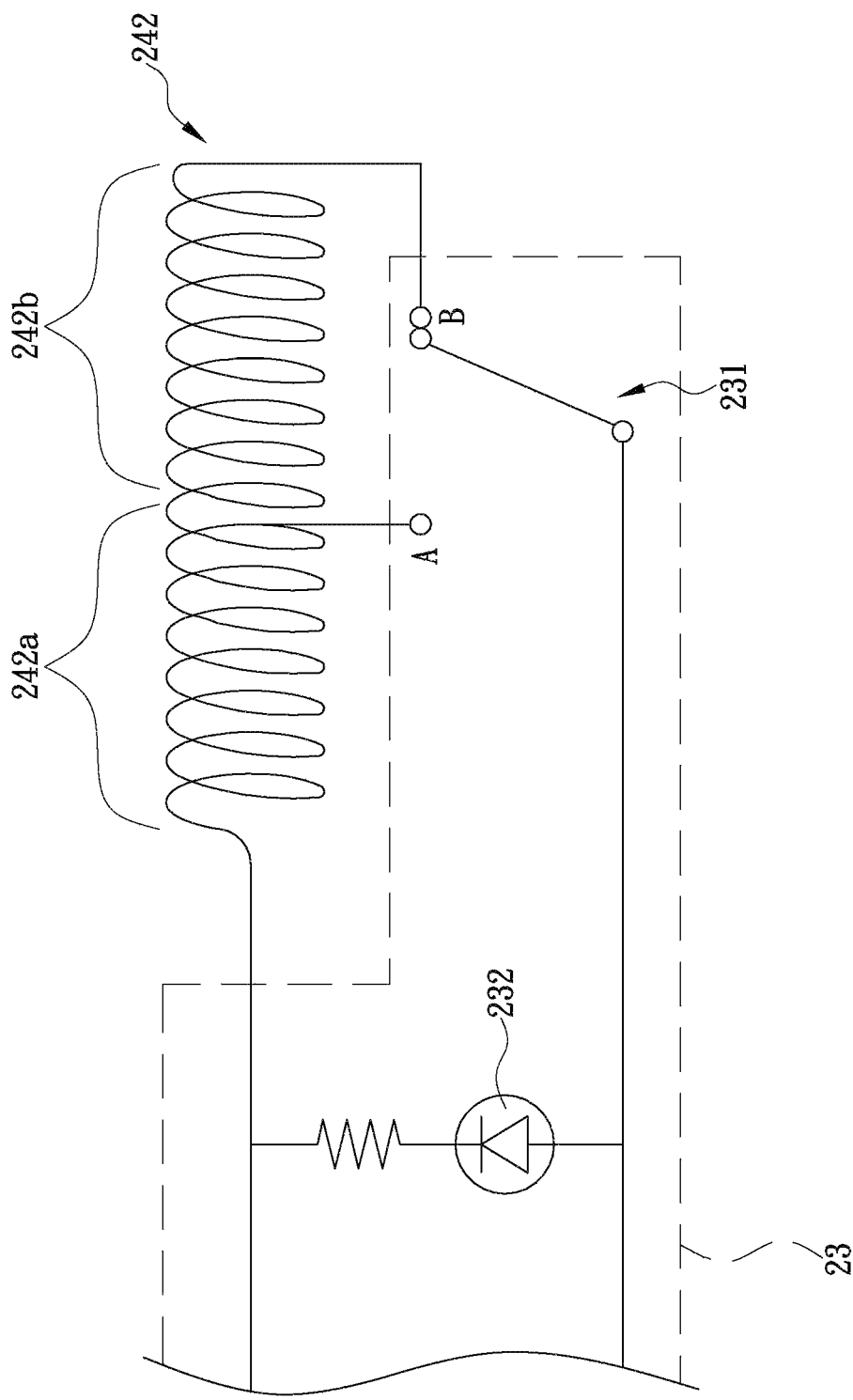
FIG. 3 is a partial schematic drawing of the second preferred embodiment of the kneading moxibustion device of the present invention.

The second preferred embodiment of the present invention is schematically shown in FIG. 3, in which elements such as the insulating member 241 and the conducting element 25 are omitted in order to more clearly explain the technical features of the embodiment. Here, the heating coil 242 is further divided into a first coil section 242a and a second coil section 242b. The first coil section 242a has one end connected to the control circuit 23 and the opposite end (hereinafter referred to as the second end of the first coil section 242a) provided with a connection terminal A. The second coil section 242b has one end connected to the second end of the first coil section 242a and the opposite end provided with a connection terminal B. In addition, the control circuit 23 is provided with a switch unit 231 and a light-emitting diode 232. While the control circuit 23 is in operation, the light-emitting diode 232 emits light in order for the user to know that the kneading moxibustion device 2 is in operation. The switch unit 231 has a movable end selectively connectable to the connection terminal A of the first coil section 242a or the connection terminal B of the second coil section 242b. The user can adjust the connection state of the switch unit 231 (e.g., through a toggle switch mounted on the base) and thereby change the heating power of the heating coil 24. For example, assume the first coil section 242a has 1000 turns and the second coil section 242b has 500 turns. When the switch unit 231 is connected to the connection terminal B of the second coil section 242b, current flows through both coil sections 242a and 242b such that the working resistance of the heating coil 24 (or the range of the alternating magnetic field generated by the heating coil 24) is increased as compared with when the switch unit 231 is connected otherwise. This connection state can keep the contact element at the optimal temperature (about 40~50° C.).

Conversely, when the switch unit 231 is connected to the connection terminal A of the first coil section 242a, current flows through only the first coil section 242a of the heating coil 242. As a result, the working resistance of the heating coil 24 (or the range of the alternating magnetic field generated by the heating coil 24) is decreased as compared with when the switch unit 231 is connected to the connection terminal B of the second coil section 242b. This connection state allows the contact element to stay at a lower temperature (about 38~40° C.) than in the foregoing connection state. Referring to FIG. 2 and FIG. 3, the user can adjust the output thermal energy of the kneading moxibustion device 2 as needed, and yet the adjusting method is not limited to the foregoing. For instance, the temperature of the outer surface of the contact element 22 can be changed by varying the strength of the electricity output by the power supply unit 20 of the kneading moxibustion device 2.

Figure 4:
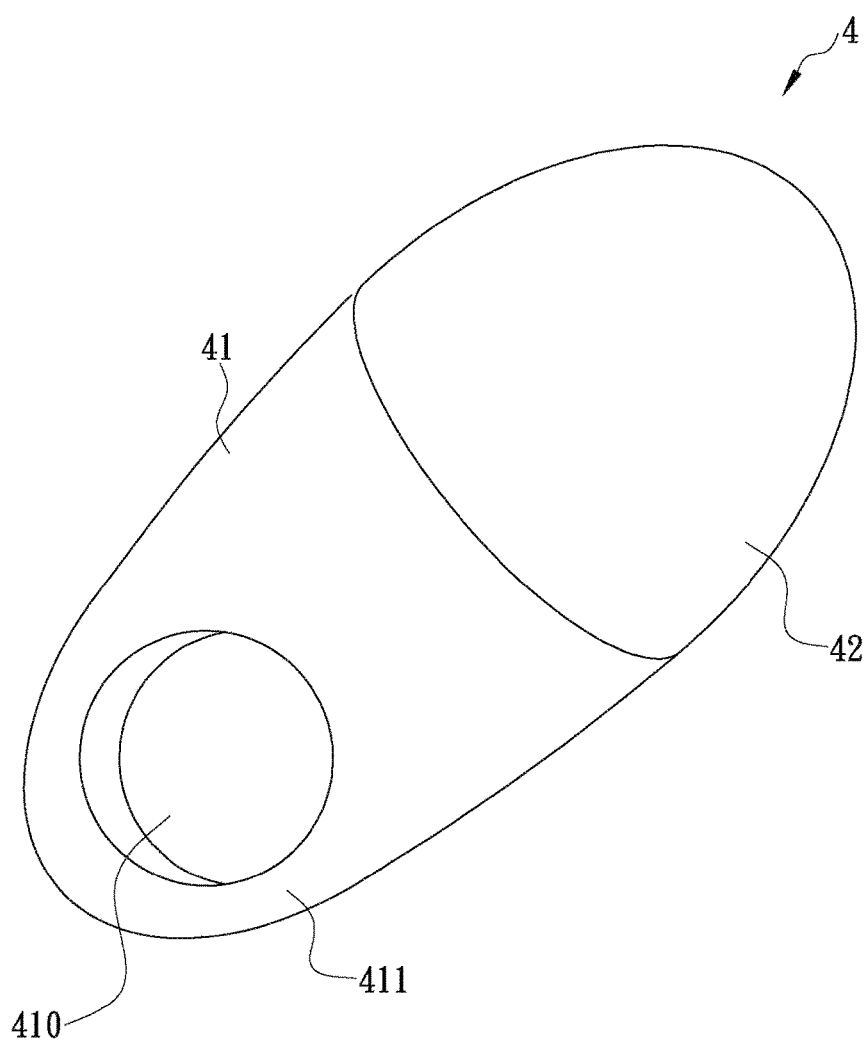
FIG. 4 schematically shows the third preferred embodiment of the kneading moxibustion device of the present invention.

The kneading moxibustion device of the present invention not only helps promote blood circulation and enhance cell regeneration, but also can relieve sore muscles, eliminate fatigue, and restore the vitality of skin. In addition, the kneading moxibustion device of the present invention is not limited to the handheld configuration shown in FIG. 2. For example, referring to FIG. 4 for the third preferred embodiment of the present invention, the base 41 of the kneading moxibustion device 4 is penetrated by an opening 410 and is thus formed with an annular portion 411 adjacent to the opening 410. The annular portion 411, into which a user can put a finger for a firm hold, serves to facilitate operation of the kneading moxibustion device 4 during moxibustion. Besides, the configuration and size of the contact element 42 can be adjusted according to practical needs.

Figure 5:
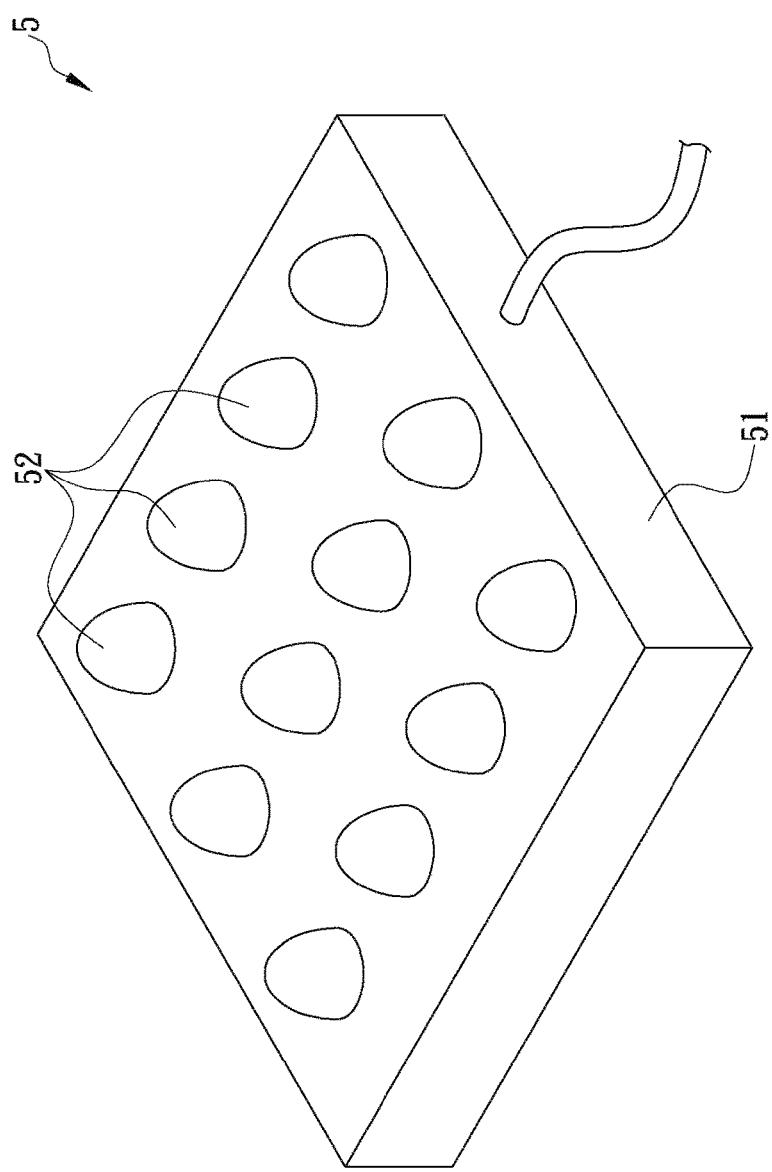
FIG. 5 schematically shows the fourth preferred embodiment of the kneading moxibustion device of the present invention.

The fourth preferred embodiment of the present invention is shown in FIG. 5, in which the kneading moxibustion device 5 has a plate-shaped base 51 mounted with a plurality of contact elements 52. A user can press a hard-to-reach body part (e.g., the sole of a foot or the back) directly against the base 51 (e.g., by stepping or lying on it) for a comfortable moxibustion session.

While the invention herein disclosed has been described by means of specific embodiments, numerous modifications and variations could be made thereto by those skilled in the art without departing from the scope of the invention set forth in the claims.

What is claimed is:

1. A kneading moxibustion device, comprising:
    a base having an end concavely provided with a receiving cavity, the base being further provided with a first assembly portion adjacent to the receiving cavity;
    a contact element made of an insulating material and having an end provided with a second assembly portion, the second assembly portion being connectable with the first assembly portion in order for the contact element to seal the receiving cavity and thereby form a sealed space therein;
    a control circuit mounted in the receiving cavity and electrically connectable with a power supply unit in order to receive electricity provided by the power supply unit and generate a driving signal according to the electricity received;
    a coil tube positioned in the sealed space and comprising an insulating member and a heating coil with a plurality of turns, the insulating member being hollow, the heating coil being wound around the insulating member and electrically connected to the control circuit in order to receive the driving signal; wherein the heating coil is divided into a first coil section and a second coil section, the first coil section having an end connected to the control circuit, the second coil section having an end connected to an opposite end of the first coil section, and the control circuit is provided with a switch unit movably connectable to the opposite end of the first coil section or an opposite end of the second coil section; wherein, when the driving signal is a direct current, the heating coil generates thermal energy in response to the direct current running through the heating coil, or when the driving signal is an alternating current, the heating coil generates an alternating magnetic field in the sealed space in response to the alternating current running through the heating coil; and
    a conducting element formed of metal and comprising an induction portion and a conduction portion, the induction portion matching the insulating member in configuration in order to be inserted into the insulating member and consequently correspond in position to the heating coil, the conduction portion having an end connected to the induction portion and an opposite end lying against an inner wall surface of the contact element in order for the thermal energy generated by the heating coil to be transferred to an outer surface of the contact element sequentially through the insulating member, the induction portion, and the conduction portion, or for the conducting element to transfer to the contact element heat generated by the conducting element in response to an induced current generated in the induction portion via electromagnetic induction by the alternating magnetic field generated by the heating coil, wherein the contact element has an opposite end provided with a curved contact surface, and the opposite end of the conduction portion is provided with a curved conducting surface matching the curved contact surface in configuration in order for the opposite end of the conduction portion to lie tightly against the inner wall surface of the contact element.

2. The kneading moxibustion device of claim 1, wherein the heating coil has 500~2500 said runs.

3. The kneading moxibustion device of claim 2, wherein the insulating member has an end provided with a stop portion, and the end of the conduction portion lies against the stop portion.

4. The kneading moxibustion device of claim 3, wherein the base is penetrated by an opening and is thus formed with an annular portion adjacent to the opening.

* * * * *